United States Patent
Ben-Ezra (10) Patent No.: US 12,350,526 B2
(45) Date of Patent: Jul. 8, 2025

(54) DOPPLER GUIDED ULTRASOUND THERAPY

(71) Applicant: NINA MEDICAL LTD, Nazareth (IL)

(72) Inventor: Shmuel Ben-Ezra, Pardes-Hanna (IL)

(73) Assignee: NINA MEDICAL LTD, Nazareth (IL)

( * ) Notice: Subject to any disclaimer, the term of this patent is extended or adjusted under 35 U.S.C. 154(b) by 0 days.

(21) Appl. No.: 16/246,522

(22) PCT Filed: Jul. 13, 2017

(86) PCT No.: PCT/IL2017/050799
§ 371 (c)(1),
(2) Date: Jan. 13, 2019

(87) PCT Pub. No.: WO2018/015944
PCT Pub. Date: Jan. 25, 2018

(65) Prior Publication Data
US 2019/0232090 A1    Aug. 1, 2019

Related U.S. Application Data (60) Provisional application No. 62/363,295, filed on Jul. 17, 2016.

(51) Int. Cl.
A61N 7/02    (2006.01)
A61B 8/00    (2006.01)
A61N 7/00    (2006.01)

(52) U.S. Cl.
CPC .............. *A61N 7/02* (2013.01); *A61B 8/485* (2013.01); *A61B 8/488* (2013.01);
(Continued)

(58) Field of Classification Search
CPC .................................. A61B 8/488; A61N 7/02
See application file for complete search history.

(56) References Cited

U.S. PATENT DOCUMENTS

| | | |
|---|---|---|
| 5,086,775 A | 2/1992 | Parker et al. |
| 5,109,857 A | 5/1992 | Roundhill et al. |
| | (Continued) | |

FOREIGN PATENT DOCUMENTS

| | | |
|---|---|---|
| KR | 20130034987 | 4/2013 |
| KR | 20170091813 A | 8/2017 |
| | (Continued) | |

OTHER PUBLICATIONS

ISR & WO received in PCT/IL2017/050799, mailed Oct. 17, 2017, 11 pages.
(Continued)

*Primary Examiner* — Anne M Kozak
*Assistant Examiner* — Aminah Asghar
(74) *Attorney, Agent, or Firm* — The Roy Gross Law Firm, LLC; Roy D. Gross (57) ABSTRACT

Apparatus is provided for assessing a characteristic of a first acoustic field (22) at a first frequency in a region (24) of a medium (26), the first acoustic field generating oscillatory motion of scatterers (28) disposed within the medium, at the first frequency. An acoustic transducer (30) (a) generates a second acoustic field (32) at a second frequency in the region, the second frequency being higher than the first frequency, and (b) receives echo data of the second acoustic field scattering off the oscillating scatterers in the medium, the echo data containing Doppler-shifted frequencies related to the oscillations of the scatterers, resulting in a time-dependent Doppler shift that oscillates at a frequency that is related to the first frequency. Control circuitry (36) (a) extracts the oscillating time-dependent Doppler shift from the received echo data, and (b) converts the extracted Doppler shift into particle-velocity of the first acoustic field.

20 Claims, 5 Drawing Sheets

(52) U.S. Cl.
CPC ................ *A61N 2007/0052* (2013.01); *A61N 2007/0073* (2013.01); *A61N 2007/0095* (2013.01)

(56) References Cited

U.S. PATENT DOCUMENTS

| | | | |
|---|---|---|---|
| 5,224,482 | A | 7/1993 | Nikoonahad et al. |
| 5,425,370 | A | 6/1995 | Vilkomerson |
| 5,472,405 | A | 12/1995 | Buchholtz et al. |
| 5,919,139 | A | 7/1999 | Lin |
| 6,086,535 | A | 7/2000 | Ishibashi et al. |
| 6,128,523 | A | 10/2000 | Bechtold |
| 6,425,867 | B1 | 7/2002 | Vaezy et al. |
| 6,454,713 | B1 | 9/2002 | Ishibashi et al. |
| 6,485,423 | B2 | 11/2002 | Angelsen et al. |
| 6,786,097 | B2 | 2/2004 | Song et al. |
| 6,875,176 | B2 | 4/2005 | Mourad et al. |
| 7,876,149 | B2 | 1/2011 | Song et al. |
| 8,337,434 | B2 | 12/2012 | Vaezy et al. |
| 8,743,657 | B1 | 6/2014 | Barton, III et al. |
| 9,107,798 | B2 | 8/2015 | Azhari et al. |
| 9,420,988 | B2 | 8/2016 | Anand et al. |
| 9,743,909 | B1 * | 8/2017 | Sapozhnikov ........... A61N 7/02 |
| 10,281,568 | B2 | 5/2019 | Oelze et al. |
| 2003/0115963 | A1 | 6/2003 | Song et al. |
| 2003/0204141 | A1 | 10/2003 | Nock et al. |
| 2004/0034304 | A1 * | 2/2004 | Sumi ..................... A61B 5/0051 600/439 |
| 2004/0034305 | A1 | 2/2004 | Song et al. |
| 2004/0267129 | A1 | 12/2004 | Angelsen et al. |
| 2005/0203399 | A1 | 9/2005 | Vaezy et al. |
| 2007/0106157 | A1 | 5/2007 | Kaczkowski et al. |
| 2007/0167774 | A1 | 7/2007 | Jeong et al. |
| 2007/0232912 | A1 | 10/2007 | Chen et al. |
| 2007/0276245 | A1 | 11/2007 | Konofagou |
| 2008/0097207 | A1 * | 4/2008 | Cai ......................... A61N 7/02 600/442 |
| 2008/0312561 | A1 | 12/2008 | Chauhan |
| 2009/0124203 | A1 | 5/2009 | Song et al. |
| 2009/0209858 | A1 | 8/2009 | Oelze |
| 2010/0160781 | A1 | 6/2010 | Carter et al. |
| 2010/0274130 | A1 | 10/2010 | Anand et al. |
| 2010/0280373 | A1 | 11/2010 | Fan et al. |
| 2010/0286514 | A1 | 11/2010 | Leighton et al. |
| 2013/0184580 | A1 | 7/2013 | Lause |
| 2014/0147013 | A1 * | 5/2014 | Shandas ................. A61B 8/481 382/107 |
| 2014/0150556 | A1 | 6/2014 | Angelsen et al. |
| 2015/0164480 | A1 | 6/2015 | Watanabe et al. |
| 2016/0120511 | A1 | 5/2016 | Azuma et al. |
| 2016/0121142 | A1 * | 5/2016 | Zhang ................. A61B 8/4263 600/439 |
| 2016/0131749 | A1 * | 5/2016 | Kim ..................... G01S 7/52074 367/7 |
| 2016/0262727 | A1 | 9/2016 | Dayton et al. |
| 2017/0080259 | A1 * | 3/2017 | Lu ....................... A61B 18/0206 |
| 2017/0360407 | A1 * | 12/2017 | Sethuraman ............. A61N 7/00 |
| 2018/0145770 | A1 | 5/2018 | Oelze et al. |
| 2019/0038253 | A1 | 2/2019 | Song et al. |
| 2019/0175139 | A1 | 6/2019 | Singh et al. |
| 2019/0290939 | A1 | 9/2019 | Watson et al. |
| 2019/0314646 | A1 | 10/2019 | Song et al. |

FOREIGN PATENT DOCUMENTS

| | | | | |
|---|---|---|---|---|
| WO | WO-2013047960 | A1 * | 4/2013 | ............... A61N 7/02 |
| WO | 2020/181290 | A1 | 9/2020 | |

OTHER PUBLICATIONS

ISR & WO received in PCT/IL2019/050089, mailed Jun. 18, 2019, 8 pages.

"Low-order complex AR models for mean and maximum frequency estimation in the context of Doppler color flow mapping" [Loupas et al., IEEE Transactions on Ultrasonics, Ferroelectrics, and Frequency Control, vol. 37, No. 6, Nov. 1990].

"An axial velocity estimator for ultrasound blood flow imaging, based on a full evaluation of the Doppler equation by means of a two-dimensional autocorrelation approach" [Loupas et al., IEEE Transactions on Ultrasonics, Ferroelectrics, and Frequency Control, vol. 42, No. 4, Jul. 1995].

"Experimental evaluation of velocity and power estimation for ultrasound blood flow imaging, by means of a two-dimensional autocorrelation approach" [Loupas et al., IEEE Transactions on Ultrasonics, Ferroelectrics, and Frequency Control, vol. 42, No. 4, Jul. 1995].

"Acoustic Radiation Force Impulse (ARFI) Imaging: a Review" [Kathy Nightingale, Curr Med Imaging Rev. Nov. 1, 2011; 7(4): 328-339].

"Developments in target micro-Doppler signatures analysis: radar imaging, ultrasound and through-the-wall radar" [Clemente et al., EURASIP Journal on Advances in Signal Processing 2013, 2013:47].

"High intensity focused ultrasound (HIFU) focal spot localization using harmonic motion imaging (HMI)" [Han et al., 2015 Phys. Med. Biol. 60 5911-5924, downloaded Sep. 13, 2016].

"Observations of tissue response to acoustic radiation force: opportunities for imaging" [Nightingale et.al., Ultrason. Imaging vol. 24, Issue 3, 2002].

"Ultrasound elastography: Principles and techniques" [Gennisson et al., Diagnostic and Interventional Imaging (2013) 94, 487-495].

Bonnefous, O., and Patrick Pesque. "Time domain formulation of pulse-Doppler ultrasound and blood velocity estimation by cross correlation." Ultrasonic imaging 8.2 (1986): 73-85.

Kasai, Chihiro, et al. "Real-time two-dimensional blood flow imaging using an autocorrelation technique." IEEE Transactions on sonics and ultrasonics 32.3 (1985): 458-464.

Jensen, Jørgen Arendt. "Implementation of ultrasound time-domain cross-correlation blood velocity estimators." IEEE transactions on biomedical engineering 40.5 (1993): 468-474.

Munk, Peter. Estimation of blood velocity vectors using ultrasound. Diss. Department of Information Technology, Technical University of Denmark, 2000.

Pulse Shapes, https://www.ldeo.columbia.edu/users/menke/radar/pulse/index.html, downloaded Jan. 21, 2018.

An Office Action summarized English translation and Search Report dated Apr. 26, 2021, which issued during the prosecution of Chinese Patent Application No. 201780055779.9.

PCT Preliminary Report for International Application No. PCT/IL2017/050799; dated Jan. 22, 2019; 5 pp.

European Search Report dated Dec. 8, 2020, which issued during the prosecution of Applicant's European App No. 17830598.3.

Real-time visualization of high-intensity focused ultrasound treatment using ultrasound imaging (Vaezy et al., Ultrasound in Med. & Biol., vol. 27, No. 1, 2001).

Hyperecho in ultrasound images of HIFU therapy: involvement of cavitation (Rabkin et al., Ultrasound in Med. & Biol., vol. 31, No. 7, 2005).

Acoustic characterization of high intensity focused ultrasound fields: A combined measurement and modeling approach (Canney et al., The Journal of the Acoustical Society of America, vol. 124, No. 4, pp. 2406-2420, Oct. 2008.

Passive cavitation imaging with ultrasound arrays (Salgaonkar et al., The Journal of the Acoustical Society of America, vol. 126, No. 6, Dec. 2009).

Passive spatial mapping of inertial cavitation during hifu exposure (Gyongy et al., IEEE Transactions on Biomedical Engineering, vol. 57, No. 1, Jan. 2010).

Combined passive detection and ultrafast active imaging of cavitation events induced by short pulses of high-intensity ultrasound (Gateau et al., IEEE Transactions on Ultrasonics, Ferroelectrics, and Frequency Control, vol. 58, No. 3, 2011).

Spatiotemporal Monitoring of High-Intensity Focused Ultrasound Therapy with Passive Acoustic Mapping (Jensen et al., Radiology: vol. 2262: No. 1, Jan. 2012).

In Vivo Application and Localization of Transcranial Focused Ultrasound Using Dual-Mode Ultrasound Arrays (Haritonova et al., (56) References Cited

OTHER PUBLICATIONS

IEEE Transactions on Ultrasonics, Ferroelectrics, and Frequency Control, vol. 62, No. 12, pp. 2031-2042, 2015).
Passive acoustic mapping utilizing optimal beamforming in ultrasound therapy monitoring (Coviello et al., The Journal of the Acoustical Society of America, vol. 137, No. 5, May 2015).
Real-time monitoring of HIFU treatment using pulse inversion (Song et al., Physics in Medicine & Biology, vol. 58, No. 15, Jul. 17, 2013).
Quantitative frequency-domain passive cavitation imaging (Haworth et al., IEEE Transactions on Ultrasonics, Ferroelectrics, and Frequency Control, vol. 64, No. 1, Jan. 2017).
In vivo real-time cavitation imaging in moving organs (Arnal et al., Physics in Medicine & Biology, vol. 62, No. 3, Jan. 10, 2017).
Supplementary European Search Report for European Application No. 19743270, issued Sep. 22, 2021, 5pp.
PCT International Search Report for International Application No. PCT/IL2021/0513001, mailed Jan. 28, 2022, 2pp.
PCT Written Opinion for International Application No. PCT/IL2021/0513001, mailed Jan. 28, 2022, 7pp.
United States Patent and Trademark Office, Non-Final Office Action for U.S. Appl. No. 16/964,057, mailed Sep. 15, 2022, 91pp.
United States Patent and Trademark Office, Final Office Action for U.S. Appl. No. 16/964,057, mailed Jun. 16, 2023, 55pp.
United States Patent and Trademark Office, Non-Final Office Action for U.S. Appl. No. 16/964,057, dated Sep. 6, 2024, 56pp.
European Patent Office, Communication pursuant to Rule 71(3) EPC—Intention to Grant and Text Intended for grant—for European Patent Application No. 19743270.1, dated Dec. 18, 2024, 38pp.

\* cited by examiner

DOPPLER GUIDED ULTRASOUND THERAPY

CROSS REFERENCE TO RELATED APPLICATIONS

The present application is a US national stage application of PCT/IL2017/050799, filed Jul. 13, 2017, which published as PCT Publication WO 2018/015944 to Ben-Ezra, and which claims the priority of U.S. 62/363,295 to Ben-Ezra, filed Jul. 17, 2016, entitled, "Doppler guided ultrasound therapy." The content of both applications is incorporated herein by reference herein in their entirety.

FIELD OF THE INVENTION

Applications of the present invention relate to acoustic field characterization, measurement, and mapping. More specifically, applications of the present invention relate to image guided therapy, such as image guided high intensity focused ultrasound (HIFU).

BACKGROUND

Ultrasound energy is often used for imaging of internal organs and tissue. High intensity focused ultrasound (HIFU), also known as high intensity therapeutic ultrasound (HITU), is a method for non-invasive treatment of internal organs and tissue, e.g., tumors.

An NIH Public Access review article dated Nov. 1, 2011, entitled "Acoustic radiation force impulse (ARFI) imaging: A review," by Kathy Nightingale, describes acoustic radiation force based elasticity imaging methods that are under investigation by many groups. Methods have been developed that utilize impulsive (i.e. <1 ms), harmonic (pulsed), and steady state radiation force excitations. The work discussed in the review article utilizes impulsive methods, for which two imaging approaches have been pursued: 1) monitoring the tissue response within the radiation force region of excitation (ROE) and generating images of relative differences in tissue stiffness (Acoustic Radiation Force Impulse (ARFI) imaging); and 2) monitoring the speed of shear wave propagation away from the ROE to quantify tissue stiffness (Shear Wave Elasticity Imaging (SWEI)). For these methods, a single ultrasound transducer on a commercial ultrasound system can be used to both generate acoustic radiation force in tissue, and to monitor the tissue displacement response. The response of tissue to this transient excitation is described as being complicated and depending upon tissue geometry, radiation force field geometry, and tissue mechanical and acoustic properties. Higher shear wave speeds and smaller displacements are associated with stiffer tissues, and slower shear wave speeds and larger displacements occur with more compliant tissues. ARFI imaging is described in the article as having spatial resolution comparable to that of B-mode, often with greater contrast, providing matched, adjunctive information. SWEI images are described as having quantitative information about the tissue stiffness, typically with lower spatial resolution.

A 2013 EURASIP Journal on Advances in Signal Processing review article entitled "Developments in target micro-Doppler signature analysis: radar imaging, ultrasound and through-the-wall radar," by Carmine Clemente et al., describes how target motions, other than the main bulk translation of the target, induce Doppler modulations around the main Doppler shift that form what is commonly called a target micro-Doppler signature. Radar micro-Doppler signatures are generally both target and action specific and hence can be used to classify and recognize targets as well as to identify possible threats. In recent years, research into the use of micro-Doppler signatures for target classification to address many defense and security challenges has been of increasing interest. The article presents a review of the work published in the last 10 years on emerging applications of radar target analysis using micro-Doppler signatures. Specifically, the article reviews micro-Doppler target signatures in bistatic. SAR and ISAR, through-the-wall radar and ultrasound radar.

US 2007/0232912 to Chen describes a non-invasive positioning system for determining the focus location of a HIFU device, the positioning system including a diagnostic ultrasound and the HIFU for ablating and removing tumor tissue. The imaging plane of the diagnostic ultrasound probe and the geometrical axis of a probe of the HIFU define an inclining angle during operation. When the imaging plane of the diagnostic ultrasound intersects the focus of the HIFU energy transducer, a maximal convergent interference signals is obtained, so as to position the HIFU focus within tumors for precise ablation.

SUMMARY OF THE INVENTION

Apparatus is provided and a method is described for assessing a characteristic, e.g., particle-velocity, of an acoustic field, in accordance with some applications of the present invention. A first acoustic transducer generates a first acoustic field at a first frequency in a region of a medium, which generates oscillatory motion of scatterers disposed within the medium in the region. The oscillatory motion of these particles is known as the particle-velocity of the acoustic field and the oscillations occur at the frequency of the first acoustic field. A second acoustic transducer generates a second acoustic field at a second frequency that is higher than the first frequency. The second acoustic field scatters off the oscillating scatterers in the medium such that echo data of the second field contains Doppler-shifted frequencies that relate to the oscillations of the scatterers. The result is a time-dependent Doppler shift that oscillates at a frequency related, e.g., substantially equal, to the first frequency. The second acoustic transducer receives the echo data, and control circuitry is used to extract the oscillating time-dependent Doppler shift and convert it into particle-velocity of the first acoustic field.

In accordance with some applications of the present invention, apparatus is provided for determining the location and size of a focal region of HIFU energy emitted at a first frequency into a region in a medium. Location and size of the focal region can be determined by mapping the particle-velocity of the acoustic field generated by the HIFU energy using a second acoustic field that is transmitted as a pulsed wave at a second frequency that is higher than the first frequency. Imaging ultrasound may be used for guidance of the focal region during treatment. A first acoustic transducer emits HIFU energy to generate a first acoustic field in the region, generating oscillatory motion of scatterers in the region, and an acoustic probe is used for imaging ultrasound, generating the second acoustic field, and receiving echo data of the second acoustic field scattering off the scatterers. Control circuitry is used to (a) generate a real-time sonogram of the medium. (b) extract an oscillating time-dependent Doppler shift from the echo data, (c) convert the extracted Doppler shift into particle-velocity of the first acoustic field in the region, and (d) generate a map of particle-velocities on a portion of the sonogram corresponding to the region. The area within the region having the highest particle-velocity corresponds to the area where the intensity of the HIFU energy is the highest, i.e., the focal region of the HIFU energy.

There is therefore provided, in accordance with some applications of the present invention, apparatus for assessing a characteristic of a first acoustic field at a first frequency in a region of a medium, the first acoustic field generating oscillatory motion of scatterers disposed within the medium, at the first frequency, the apparatus including:

an acoustic transducer configured to (a) generate a second acoustic field at a second frequency in the region of the medium, the second frequency being higher than the first frequency, and (b) receive echo data of the second acoustic field scattering off the oscillating scatterers in the medium, the echo data containing Doppler-shifted frequencies related to the oscillatory motion of the scatterers, resulting in a time-dependent Doppler shift that oscillates at a frequency that is related to the first frequency; and control circuitry configured to (a) extract the oscillating time-dependent Doppler shift from the received echo data, and (b) convert the extracted Doppler shift into particle-velocity of the first acoustic field.

For some applications, the apparatus further includes an ultrasound transducer, the ultrasound transducer being configured to generate the first acoustic field.

For some applications, the control circuitry is further configured to derive at least one parameter of the first acoustic field from the particle-velocity of the first acoustic field.

For some applications, the acoustic transducer is configured to generate the second acoustic field by transmitting a pulsed acoustic wave into the region of the medium.

For some applications, the control circuitry is configured to generate a two-dimensional image based on the received echo data of the second acoustic field scattering off the scatterers.

There is further provided, in accordance with some applications of the present invention, a method for assessing a characteristic of an acoustic field, the method including:

generating a first acoustic field at a first frequency in a region of a medium, the first acoustic field generating oscillatory motion of scatterers disposed within the medium in the region, the scatterers oscillating at the first frequency;

generating a second acoustic field at a second frequency in the region of the medium, wherein the second frequency is higher than the first frequency;

receiving echo data of the second acoustic field scattering off the scatterers, the echo data containing Doppler-shifted frequencies related to the oscillatory motion of the scatterers, resulting in a time-dependent Doppler shift that oscillates at a frequency that is related to the first frequency;

extracting the oscillating time-dependent Doppler shift from the received echo data; and converting the extracted Doppler shift into particle-velocity of the first acoustic field.

For some applications, the method further includes deriving at least one parameter of the first acoustic field from the particle-velocity.

For some applications, generating the second acoustic field includes generating a second acoustic field at a second frequency, the second frequency being 3 to 25 times higher than the first frequency.

For some applications, generating the second acoustic field includes generating a second acoustic field at a second frequency, the second frequency being 5 to 25 times higher than the first frequency.

For some applications, generating the second acoustic field includes generating a second acoustic field at a second frequency, the second frequency being 5 to 10 times higher than the first frequency.

For some applications, generating the first acoustic field includes emitting high intensity focused ultrasound (HIFU) energy into the region of the medium.

For some applications, generating the second acoustic field includes transmitting a pulsed acoustic wave into the region of the medium.

For some applications, the method further includes generating a two-dimensional image based on the received echo data of the second acoustic field scattering off the scatterers.

There is further provided, in accordance with some applications of the present invention, apparatus for assessing a characteristic of an acoustic field, the apparatus including:

a first acoustic transducer configured to generate a first acoustic field at a first frequency in a region of a medium, the first acoustic field generating oscillatory motion of scatterers disposed within the medium in the region, the scatterers oscillating at the first frequency;

a second acoustic transducer configured to (a) generate a second acoustic field at a second frequency in the region of the medium, the second frequency being higher than the first frequency, and (b) receive echo data of the second acoustic field scattering off the scatterers, the echo data containing Doppler-shifted frequencies related to the oscillatory motion of the scatterers, resulting in a time-dependent Doppler shift that oscillates at a frequency that is related to the first frequency; and control circuitry configured to (a) extract the oscillating time-dependent Doppler shift from the received echo data, and (b) convert the extracted Doppler shift into particle-velocity of the first acoustic field.

For some applications, the control circuitry is further configured to derive at least one parameter of the first acoustic field from the particle-velocity of the first acoustic field.

For some applications, the second acoustic transducer is configured to generate the second acoustic field at a second frequency, the second frequency being 3 to 25 times higher than the first frequency.

For some applications, the second acoustic transducer is configured to generate the second acoustic field at a second frequency, the second frequency being 5 to 25 times higher than the first frequency.

For some applications, the second acoustic transducer is configured to generate the second acoustic field at a second frequency, the second frequency being 5 to 10 times higher than the first frequency.

For some applications, the first acoustic transducer is configured to generate the first acoustic field by emitting high intensity focused ultrasound (HIFU) energy into the region of the medium.

For some applications, the apparatus further comprises a single housing to which the first and second acoustic transducers are coupled, the housing aligning the first and second acoustic fields to be parallel or anti-parallel.

For some applications, the second acoustic transducer is configured to generate the second acoustic field by transmitting a pulsed acoustic wave into the region of the medium.

For some applications, the control circuitry is configured to generate a two-dimensional image based on the received echo data of the second acoustic field scattering off the scatterers.

There is further provided, in accordance with some applications of the present invention, apparatus for use with a focal region of high intensity focused ultrasound (HIFU) energy, the apparatus including:

(A) an ultrasound transducer configured to generate a first acoustic field by emitting the HIFU energy into a region of a medium at a first frequency, the first acoustic field generating oscillatory motion of scatterers disposed within the medium in the region, the scatterers oscillating at the first frequency;

(B) an acoustic probe,
the acoustic probe being configured to emit pulse-echo ultrasound energy into the medium at an imaging frequency,
wherein an acoustic element selected from the group consisting of the ultrasound transducer and the acoustic probe is configured to generate a second acoustic field by transmitting a pulsed acoustic wave into the region at a second frequency,
wherein the second frequency is higher than the first frequency and wherein the second acoustic field scatters off the scatterers at Doppler-shifted frequencies that are related to the oscillatory motion of the scatterers, resulting in echo data containing a time-dependent Doppler shift that oscillates at a frequency that is related to the first frequency, and
the acoustic probe being further configured to receive the echo data of the second acoustic field scattering off the scatterers; and (C) control circuitry configured to (a) generate a real-time sonogram of the medium from reflections of the pulse-echo ultrasound energy, (b) extract the oscillating time-dependent Doppler shift from the received echo data, (c) convert the extracted Doppler shift into particle-velocity of the first acoustic field in the region, and (d) generate a map of particle-velocities on a portion of the sonogram corresponding to the region.

For some applications, the acoustic element includes the ultrasound transducer.

For some applications, the acoustic element includes the acoustic probe.

For some applications, the first frequency is 0.1-5 MHz.

For some applications, the second frequency is 3 to 25 times higher than the first frequency.

For some applications, the second frequency is 5 to 25 times higher than the first frequency.

For some applications, the second frequency is 5 to 10 times higher than the first frequency.

For some applications, the control circuitry is configured to synchronize the first and second acoustic fields.

For some applications, the medium is tissue of a body of a subject and the transducer is configured to cause a therapeutic effect in the tissue by emitting the HIFU energy into the tissue.

For some applications, the transducer is configured to cause the therapeutic effect in the tissue by heating the tissue.

For some applications, the control circuitry is further configured to:
monitor a change in a characteristic of the tissue by monitoring a time variation of the Doppler shift; and
in response to the monitoring, terminate the first acoustic field when the characteristic of the tissue reaches a threshold value.

For some applications, the characteristic of the tissue is mechanical impedance of the tissue, and wherein the control circuitry is configured to (a) monitor a change in the mechanical impedance of the tissue by monitoring a time variation of the Doppler shift, and (b) in response to the monitoring, terminate the first acoustic field when the mechanical impedance of the tissue reaches a threshold value.

For some applications, the control circuitry is configured to monitor the change in the characteristic over a time period that is 1-120 seconds long.

For some applications:
the transducer is configured to operate in distinct calibration and therapy modes to facilitate application of therapeutic HIFU energy to a target location, in each of the modes emitting the HIFU energy with one or more differing respective parameters, and
the control circuitry is configured to vary the one or more respective parameters such that when the transducer operates in the therapeutic mode the HIFU energy causes a therapeutic effect in the tissue whereas when the transducer is operating in the calibration mode the HIFU energy does not cause a therapeutic effect in the tissue.

For some applications, the control circuitry is configured to vary a duration of a pulse of the HIFU energy, such that when the transducer operates in the therapeutic mode the duration of the pulse is longer than the duration of the pulse is when the transducer operates in the calibration mode.

For some applications, the control circuitry is configured to vary a duty-cycle of the HIFU energy, such that when the transducer operates in the therapeutic mode the duty-cycle is higher than the duty-cycle is when the transducer operates in the calibration mode.

For some applications, the control circuitry is configured to vary a power of the HIFU energy, such that when the transducer operates in the therapeutic mode the power of the HIFU energy is higher than the power of the HIFU energy is when the transducer operates in the calibration mode.

For some applications, the control circuitry is configured to monitor the tissue when the transducer operates in the therapeutic mode and to vary the parameters of the therapeutic mode according to the monitoring in order to alter an effect on the tissue.

For some applications, the apparatus includes a targeting unit configured to move the focal region of the HIFU energy.

For some applications, the targeting unit is configured such that manual movement of the targeting unit moves the focal region of the HIFU energy within the medium by moving the transducer with respect to the medium.

For some applications, the targeting unit includes (i) a transducer controller and (ii) targeting circuitry configured to (a) obtain data corresponding to the focal region of the HIFU energy on the map of particle-velocities, (b) obtain data corresponding to a target location in the medium, and (c) send an electric signal to the transducer controller, the transducer controller being configured to receive the electric signal and in response thereto move the focal region of the HIFU energy toward the target location within the medium.

For some applications, the transducer controller is configured to (a) move the focal region of the HIFU energy with respect to the transducer, and (b) change a size of the focal region of the HIFU energy by applying phased-array control to the HIFU energy emitted by the transducer.

For some applications, the transducer controller is configured to move the focal region of the HIFU energy by moving the transducer with respect to the medium.

For some applications, the apparatus further includes a single housing to which the ultrasound transducer and the acoustic probe are coupled, wherein the housing aligns the first and second acoustic fields to be parallel or anti-parallel.

The present invention will be more fully understood from the following detailed description of applications thereof, taken together with the drawings, in which:

DETAILED DESCRIPTION

An acoustic field propagating in a medium generates oscillatory motion of particles, or scatterers, within the medium. The oscillatory motion of these scatterers is known as the particle-velocity of the acoustic field and the oscillations occur at the frequency of the acoustic field. The intensity of the acoustic field relates to the maximum velocity or velocity-amplitude of the oscillating scatterers. Therefore, in a region of higher intensity the velocity-amplitude of the oscillating scatterers is higher than the velocity-amplitude of the oscillating scatterers is in a region of lower intensity, i.e., the particle-velocity of the acoustic field is highest in the region of highest intensity within the field.

Intensity of the acoustic field is the product of pressure p and particle-velocity u, as given by the following equation:

$$I(t)=p(t)u(t),\qquad\text{[Equation 1]}$$

where I is the instantaneous intensity at some position in space, p is the pressure, and u is the particle-velocity at that position.

The local complex mechanical impedance Z of the medium is defined by:

$$Z=p/u,\qquad\text{[Equation 2]}$$

where p and u are the complex amplitudes of harmonic waves of pressure and particle-velocity correspondingly, at a specific frequency. Mechanical impedance Z is a characteristic of the medium, and it may be position-dependent and frequency-dependent. An illustrative example, utilizing numbers that are close to those of diagnostic ultrasound, is as follows:

Z=1.5 MRayl, pressure amplitude p=1.5 MPa, and therefore particle-velocity amplitude u=1.5 [MPa]/1.5 [MRayl.]=1 [m/s].

The time-averaged intensity of the acoustic field can be written in the form:

$$I=p^2/(2Z),\qquad\text{[Equation 3]}$$

providing intensity I in terms of pressure amplitude p. Equivalently pressure p can be substituted in Equation 3 by the product of impedance Z and particle-velocity u to derive $$I=Zu^2/2\qquad\text{[Equation 4]}$$

which gives intensity I in terms of particle-velocity u.

Particle-velocity u is a function of intensity I and impedance Z, as given by the following equation:

$$u=\text{sqrt}(2I/Z),\qquad\text{[Equation 5]}$$

thus, for a given intensity I, changes in impedance Z will result in a change in particle-velocity u.

Figure 1:
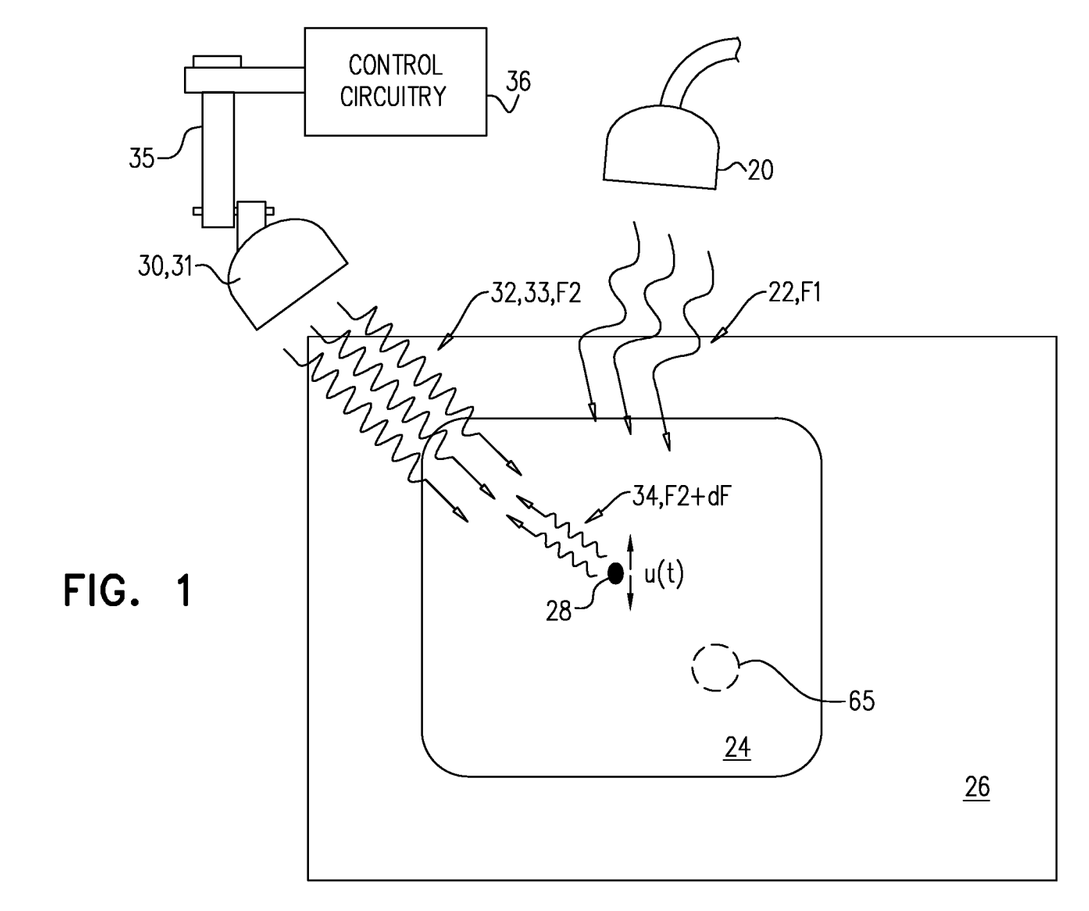
FIG. 1 is a schematic illustration of a medium, two acoustic fields in the medium, and an oscillating scatterer in the medium, according to some applications of the present invention.

Reference is now made to FIG. 1, which is a schematic illustration of a medium, a scatterer within the medium, and two acoustic fields, in accordance with some applications of the present invention. A first acoustic transducer 20 generates a first acoustic field 22, e.g., by emitting high intensity focused ultrasound (HIFU) energy, at a first frequency F1 in a region 24 of a medium 26. First acoustic field 22 generates oscillatory motion of scatterers, such as scatterer 28, disposed within medium 26 in region 24. The oscillations of the scatterers is the particle-velocity of first acoustic field 22, and is a fundamental characteristic of the acoustic field. The scatterers have time-dependent velocities u(t) and oscillate at first frequency F1. A second acoustic transducer 30 generates a second acoustic field 32 at a second frequency F2 into region 24 in medium 26. Second frequency F2 is typically higher than first frequency F1, e.g., at least 3 and/or less than 25 times higher, e.g., at least 5 and/or less than 25 times higher, e.g., at least 5 and/or less than 10 times higher.

Second acoustic field 32 scatters off the scatterers, producing echo data that contains Doppler-shifted frequencies F2+dF that are related to the oscillations of the scatterers. Second acoustic transducer 30 is configured to receive the echo data, e.g., backscatter 34 of second acoustic field 32. Due to the Doppler shift occurring from scatter off a particle that is oscillating at first frequency F1, the Doppler shift itself oscillates, resulting in an oscillating time-dependent Doppler shift dF that oscillates at a frequency that is related to, e.g., substantially equal to, first frequency F1. At any given location in region 24 the magnitude of oscillating time-dependent Doppler shift dF is proportional to the parallel component of the magnitude of the particle-velocity of first acoustic field 22 at that location. The relationship between oscillating time-dependent Doppler shift dF and the particle-velocity of first acoustic field 22 is given by the following equation:

$$dF=2*F2*U/c\qquad\text{[Equation 6]}$$

where U is the parallel component of the time-dependent velocity u(t) of scatterer 28. Control circuitry 36 is then used to (a) extract oscillating time-dependent Doppler shift dF from the received echo data and (b) convert it into particle-velocity of first acoustic field 22. For example, control circuitry 36 may consult a look-up table to determine the particle-velocity or, alternatively, it may analytically solve for the particle-velocity based on the extracted oscillating time-dependent Doppler shift dF.

For some applications, first acoustic transducer 20 and second acoustic transducer 30 are coupled to a single housing (such as housing 40 shown in FIG. 4), which aligns first acoustic field 22 and second acoustic field 32 to be either parallel or antiparallel.

It is noted that an apparatus may be sold including second acoustic transducer 30 and control circuitry 36 but not first acoustic transducer 20. Such an apparatus would have all the same properties as described above. In such a case, second acoustic transducer 30 together with control circuitry 36 may be used to assess a characteristic, e.g., particle-velocity, of an already-existing first acoustic field.

For some applications, the received echo data can be processed into a one-dimensional or two-dimensional image, depicting a map of first acoustic field 22, e.g., in terms of particle-velocity. A one-dimensional map shows a characteristic value, or a set of values, related to first acoustic field 22, plotted versus the distance along one dimension, usually defined by the propagation of second acoustic field 32. For example, the power spectrum of first acoustic field 22 may be plotted on a spectrogram, where the power spectrum of the signal is platted on the vertical axis, for a group of successive time steps or distances (time is usually converted into distance in pulse-echo applications) arranged in the horizontal axis. The power spectrum is derived from the signal by methods of Fourier analysis. For some applications, oscillating time-dependent Doppler shift dF, or the absolute value of oscillating time-dependent Doppler shift dF, can be displayed on a spectrogram. Furthermore, oscillating time-dependent Doppler shift dF can be converted into particle-velocity, and shown on a spectrogram with a distribution of particle-velocities shown on the vertical axis versus distance shown on the horizontal axis.

In order to generate a one-dimensional map, a single element probe 31, comprising one piezoelectric element, may be used. Single element probe 31 is configured to produce a substantially collimated beam 33 of acoustic field propagating from the probe into the medium along a pre-defined path. Spatial resolution can be achieved by pulse-echo (sometimes called A-Mode) operation of probe 31, adapted for Doppler analysis. In contrast to regular A-Mode where shorter pulses are used in order to obtain high spatial resolution, in Doppler A-Mode longer pulses are used in order to obtain higher resolution in the frequency domain. For example, the pulse can comprise between 5 and 20 periods, e.g., 10 periods. Second frequency F2 is the central frequency of the pulse. The time-delay between the transmitted pulse and the received echo defines the distance of a scatterer along the path. Therefore, only one-dimensional information regarding the spatial location of the source of the echo data (the scatterer) obtained. Various commercial diagnostic ultrasound machines have Doppler A-Mode capabilities, e.g., the PW-Doppler of Philips HD11.

For some applications, multiple one-dimensional images can be composed into one higher dimensional image, e.g., two-dimensional or three-dimensional, by a method of synthetic-aperture, where a controlled scanning of a pre-defined set of positions ('grid') is performed with probe 31, and a one-dimensional image is acquired in each point in the grid. For this purpose, the probe may be installed on a mechanical setup 35, with manual or computer control, adapted to enable accurate and controlled movement of probe 31.

For some applications, the two-dimensional map displays a single value for each echo data signal, related to a specific spatial location in first acoustic field 22, similarly to a pixel in a picture. Therefore, the echo data may be converted into a single number. This can be done by calculating a parameter from the signal that properly represents the echo data or particle-velocity of a specific location in first acoustic field 22, e.g., root-mean-squared value, variance, maximum value, peak-to-peak value, amplitude and/or phase.

For some applications, probe 31 may be, for example, a linear array probe, e.g. convex array probe, a phased array probe, or any other standard design for a diagnostic probe that is configured for beam-forming and pulse-echo operation, including color-Doppler imaging. Control circuitry 36 generates a sonogram combined with a color-Doppler and/or a power-Doppler map on top of the sonogram. Control circuitry 36 is configured to work in pulse-echo mode and to perform beam forming techniques in order to acquire the echo data from a specific location in medium 26. Usually, the same array of piezoelectric elements is used for generating the sonogram and the map: first, the sonogram is generated using pulse-echo ultrasound, and then, the Doppler analysis is performed to generate the map. While mapping first acoustic field 22 only requires the color-Doppler and/or the power-Doppler analysis, the sonogram provides guidance capabilities. For example, a target location 65, e.g., a tumor, can be seen on the sonogram, and the focal region of first acoustic field 22 can be seen on the map. When fused into one image, real-time feedback of the location of the focal region with respect to target location 65 is provided. A targeting unit, such as is shown in FIG. 3 may be used to move the focal region to target location 65.

For some applications, first acoustic field 22 and second acoustic field 32 are synchronized, for example, by a synchronization channel between control circuitry 36 and first acoustic field 22 (not shown). Synchronization between the first and second acoustic fields provides a controllable phase difference between the two acoustic fields. Therefore, the echo data scattering off scatterers in a specific location in first acoustic field 22, from separate pulses of second acoustic field 32, e.g., successive pulses, carry substantially the same oscillating time-dependent Doppler shift dF since the scatterers in that specific location performed substantially the same oscillatory motion under the influence of first acoustic field 22 during the successive pulses.

Figure 2A:
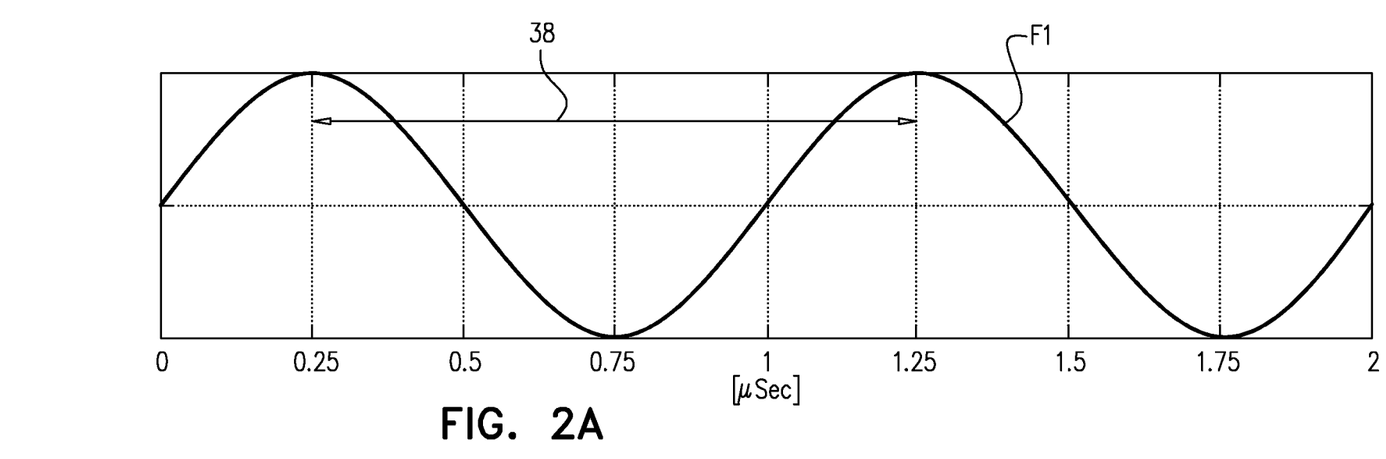
FIGS. 2A-B are graphs showing a mathematical model of the frequency of the first acoustic field, the frequency of the second acoustic field, and the shifted frequency of the second acoustic field scattering off the scatterers in the medium.
Figure 2B:
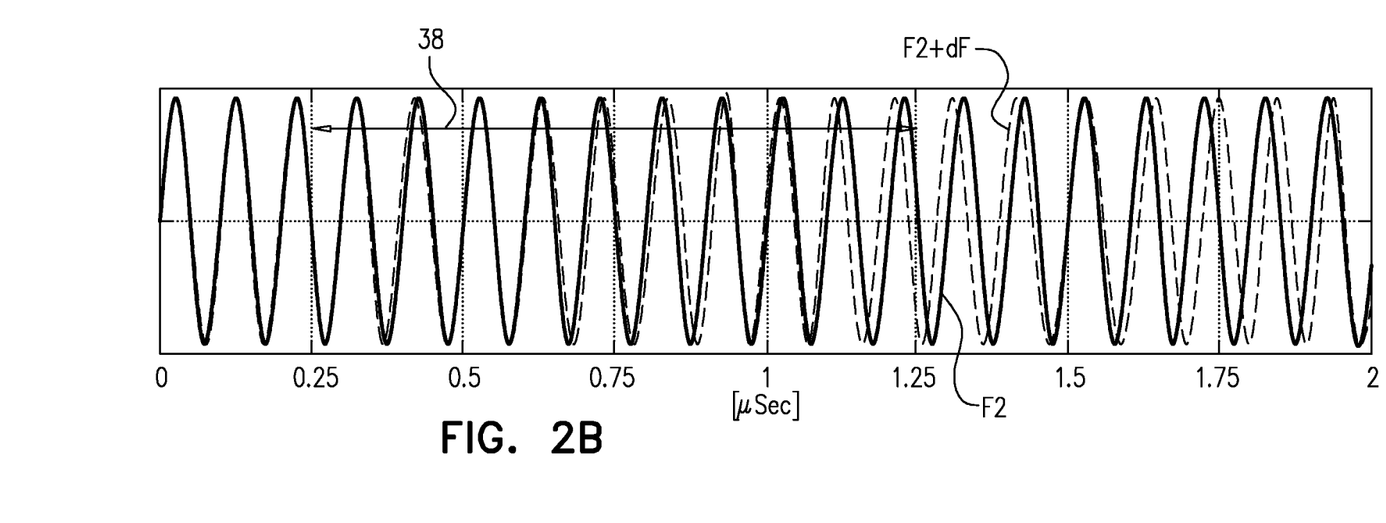

Reference is now made to FIGS. 2A-B. FIG. 2A is a graph showing a mathematical model of first frequency F1 of first acoustic field 22. FIG. 2B is a graph showing second frequency F2 of second acoustic field 32, as well as shifted frequency F2+dF of scatter, e.g., backscatter 34 from second acoustic field 32 scattering off scatterers, such as scatterer 28, in medium 26. Second frequency F2 is denoted by the solid sinusoid, and shifted frequency F2+F is denoted by the dashed sinusoid. Arrows 38 mark the time-span on each graph of one wavelength of first acoustic field 22. As can be seen in FIG. 2B, shifted frequency F2+dF oscillates with respect to second frequency F2. For example, at around 0.5 microseconds, second frequency F2 and shifted frequency F2+dF are synchronized; at around 0.75 microseconds, shifted frequency F2+dF lags behind second frequency F2; at around 1 microsecond second frequency F2 and shifted frequency F2+dF are again synchronized; and at around 1.25 microseconds, shifted frequency F2+dF precedes second frequency F2. The frequency at which F2+dF oscillates is related to, e.g., substantially equal to, first frequency F1. The magnitude of oscillating time-dependent Doppler shift dF, i.e., the amount of deviation in frequency from F2, is related to the parallel component U of time-dependent velocity u(t) of the scatterer at the time of scattering, as shown by Equation 6.

Figure 3:
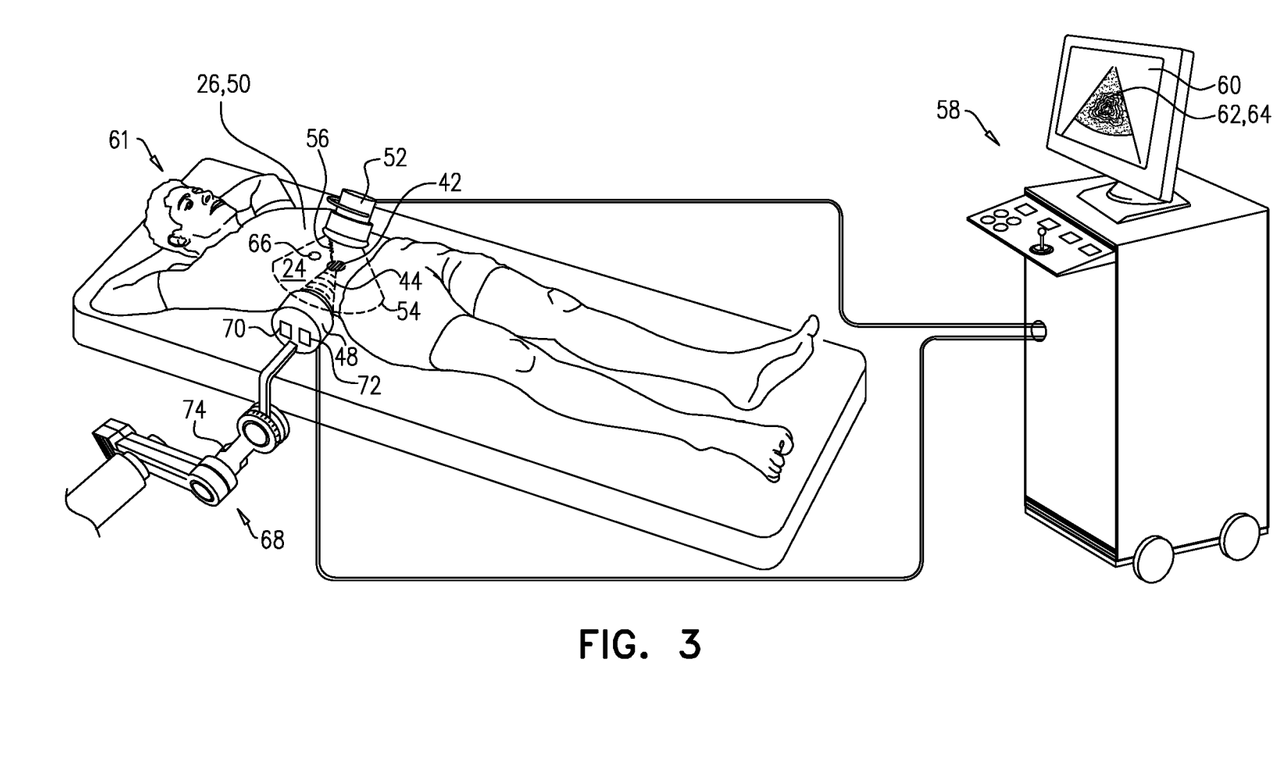
FIG. 3 is a schematic illustration of a high intensity focused ultrasound (HIFU) transducer and an acoustic probe both placed against skin of a subject, according to some applications of the present invention.

Reference is now made to FIG. 3, which is a schematic illustration of a HIFU transducer and an acoustic probe both placed against skin of a subject, according to some applications of the present invention. Apparatus is provided for determining in real-time the location and size of a focal region 42 of a beam of HIFU energy 44 within region 24 of medium 26. It is noted that described hereinbelow is a method for locating focal region 42 in real-time without the use of magnetic resonance imaging (MRI), (MRI is a more expensive way of achieving a corresponding result.) An ultrasound transducer 48 generates first acoustic field 22 (such as is shown in FIG. 1) into region 24 of medium 26 of a subject, by emitting HIFU energy 44 into region 24 at first frequency F1. HIFU energy 44 generates oscillatory motion of scatterers within medium 26, e.g., tissue 50, the scatterers oscillating at first frequency F1. Typically, ultrasound transducer 48 emits HIFU energy 44 at a frequency of at least 0.1 MHz and/or less than 5 MHz. An acoustic probe 52 emits pulse-echo ultrasound energy 54 into medium 26 at an imaging frequency. Second acoustic field 32 (such as is shown in FIG. 1) is generated in region 24 of medium 26 by either ultrasound transducer 48 or acoustic probe 52 transmitting a pulsed acoustic wave 56 into region 24 at second frequency F2. (It is rioted that all options that are described with respect to the second acoustic field being transmitted by either ultrasound transducer 48 or acoustic probe 52 are interchangeable). Second frequency F2 is typically higher, e.g., at least 3 and/or less than 25 times higher, e.g., at least 5 and/or less than 25 times higher, e.g., at least 5 and/or less than 10 times higher, than first frequency F1 of HIFU energy 44. Second acoustic field 32 scatters off scatterers in medium 26, resulting in echo data containing time-dependent Doppler shift dF that oscillates at a frequency that is related to the first frequency F1 of HIFU energy 44. Acoustic probe 52 receives the echo data, e.g., backscatter 34 as shown in FIG. 1, of second acoustic field 32 scattering.

Control circuitry 58 is configured to (a) generate a real-time sonogram 60 of medium 26 from reflections of pulse-echo ultrasound energy 54, (b) extract oscillating time-dependent Doppler shift dF from the received echo data, (c) convert extracted oscillating time-dependent Doppler shift dF into the particle-velocity of first acoustic field 22 in region 24, and (d) generate a map 62 of particle-velocities on a portion 64 of sonogram 60 that corresponds to region 24. Map 62 shows where the particle-velocity of first acoustic field 22 is highest, thereby showing where the intensity of first acoustic field 22 is highest, i.e., where focal region 42 is. Due to map 62 being overlaid on top of sonogram 60 of medium 26, focal region 42 can be seen with respect to region 24 in medium 26. Focal region 42 can then be relocated, for example by using a targeting unit as described hereinbelow, as necessary so as to focus HIFU energy 44 on target location 66 within region 24 of medium 26. For some applications control circuitry 58 may also synchronize first acoustic field 22 and second acoustic field 32. FIG. 3 shows a schematic illustration of a velocity map 62.

For some applications, medium 26 is tissue 50 of a subject 61 (FIG. 3). Ultrasound transducer 48 causes a therapeutic effect in tissue 50 by emitting HIFU energy 44 into tissue 50. For some applications, the therapeutic affect is caused by HIFU energy 44 heating tissue 50. Other, non-thermal therapeutic effects can be caused by HIFU energy 44 as well, such as, for example, cavitation, tissue liquefaction, cell necrosis, and cell apoptosis.

For some applications, control circuitry 58 is also configured to monitor a change in a characteristic of tissue 50 by monitoring a time variation of oscillating time-dependent Doppler shift dF over a time period of at least 1 and/or less than 120 seconds. When the characteristic of tissue 50 being monitored reaches a threshold value, control circuitry 58 terminates transmission of HIFU energy 44. For example, due to exposure to HIFU energy 44 the mechanical impedance of tissue 50 changes. As the mechanical impedance of tissue 50 changes, oscillating time-dependent Doppler shift dF changes as well. When the mechanical impedance of tissue 50 reaches a threshold value, control circuitry 58 terminates transmission of HIFU energy 44 into tissue 50.

In order to facilitate application of HIFU energy 44 to target location 66 in tissue 50, ultrasound transducer 48 may be configured to operate in distinct calibration and therapy modes. In each of the triodes ultrasound transducer 48 emits HIFU energy 44 with one or more differing respective parameters. Control circuitry 58 is configured to vary the respective parameters of the calibration and therapeutic modes such that when ultrasound transducer 48 operates in the therapeutic mode HIFU energy 44 causes a therapeutic effect in tissue 50, whereas when ultrasound transducer 48 operates in the calibration mode HIFU energy 44 does not cause a therapeutic effect in tissue 50. For example, control circuitry 58 may vary one or more parameters from the following set:
  a duration of a pulse of HIFU energy 44, such that when ultrasound transducer 48 operates in the therapeutic mode the duration of the pulse is longer than the duration of the pulse when ultrasound transducer 48 operates in the calibration mode,
  a duty-cycle of HIFU energy 44, such that when ultrasound transducer 48 operates in the therapeutic mode the duty-cycle is higher than the duty-cycle is when ultrasound transducer 48 operates in the calibration mode, and/or
  the power of HIFU energy 44, such that when ultrasound transducer 48 operates in the therapeutic mode the power of HIFU energy 44 is higher than the power of HIFU energy 44 when ultrasound transducer 48 operates in the calibration mode.

Operating ultrasound transducer 48 in calibration mode allows the particle-velocity of first acoustic field 22 to be mapped and focal region 42 located while not causing any damage to tissue 50. The beam of HIFU energy 44 can then be reoriented in order to relocate focal region 42, and/or the size of focal region 42 can be changed such that target location 66 is inside focal region 42. Thus, focal region 42 can be monitored and guided while ultrasound transducer 48 is in calibration mode, and once focal region 42 is in the right location, ultrasound transducer 48 can be switched to therapeutic mode in order for HIFU energy 44 to cause a therapeutic effect in tissue 50. For some applications, control circuitry 58 is configured to monitor tissue 50 while ultrasound transducer 48 operates in therapeutic mode in order to monitor how treatment is progressing. If appropriate, control circuitry 58 may vary the abovementioned parameters of ultrasound transducer 48 while it is operating in therapeutic mode in order to alter an effect on tissue 50 during treatment.

A targeting unit 68 may be used to move focal region 42 of HIFU energy 44. For some applications, targeting unit 68 is configured such that manual movement, e.g., by an operator of ultrasound transducer 48, moves ultrasound transducer 48 with respect to medium 26, thereby moving focal region 42 of HIFU energy 44 within medium 26.

Alternatively or additionally, targeting unit 68 may comprise a transducer controller 70 and targeting circuitry 72. Targeting circuitry 72 is configured to (a) obtain data corresponding to the location of focal region 42 of HIFU energy 44 on map 62 of particle-velocities, (b) obtain data corresponding to target location 66 in medium 26, and (c) send an electric signal to transducer controller 70. Transducer controller 70 receives the electric signal and in response thereto moves focal region 42 of HIFU energy 44 toward target location 66 within medium 26. For example, transducer controller 70 may move focal region 42 and/or change a size of focal region 42 by (a) applying phased-array control to HIFU energy 44, or (b) by moving ultrasound transducer 48 with respect to medium 26, e.g., by using a robotic arm 74 to move ultrasound transducer 48 with respect to medium 26. For some applications, targeting circuitry 72 may (a) obtain the data corresponding to the location of focal region 42 and target location 66 directly from control circuitry 58, thereby providing closed loop control of the treatment, i.e., control circuitry 58 sends data corresponding to the relative positions of focal region 42 and target location 66 to targeting unit 68, via targeting circuitry 72, and targeting unit 68 responds accordingly to bring focal region 42 to target location 66.

Alternatively or additionally, targeting circuitry 72 may (a) obtain real-time data from control circuitry 58 corresponding to a size of focal region 42 and (b) send the data to transducer controller 70, such that transducer controller 70 may change a size of focal region 42 in order to focus or defocus HIFU energy 44. For example, the size of focal region 42 may be (a) decreased in order to increase the intensity of HIFU energy 44 in focal region 42, or (b) increased in order to decrease the intensity of HIFU energy 44 in focal region 42.

Figure 5:
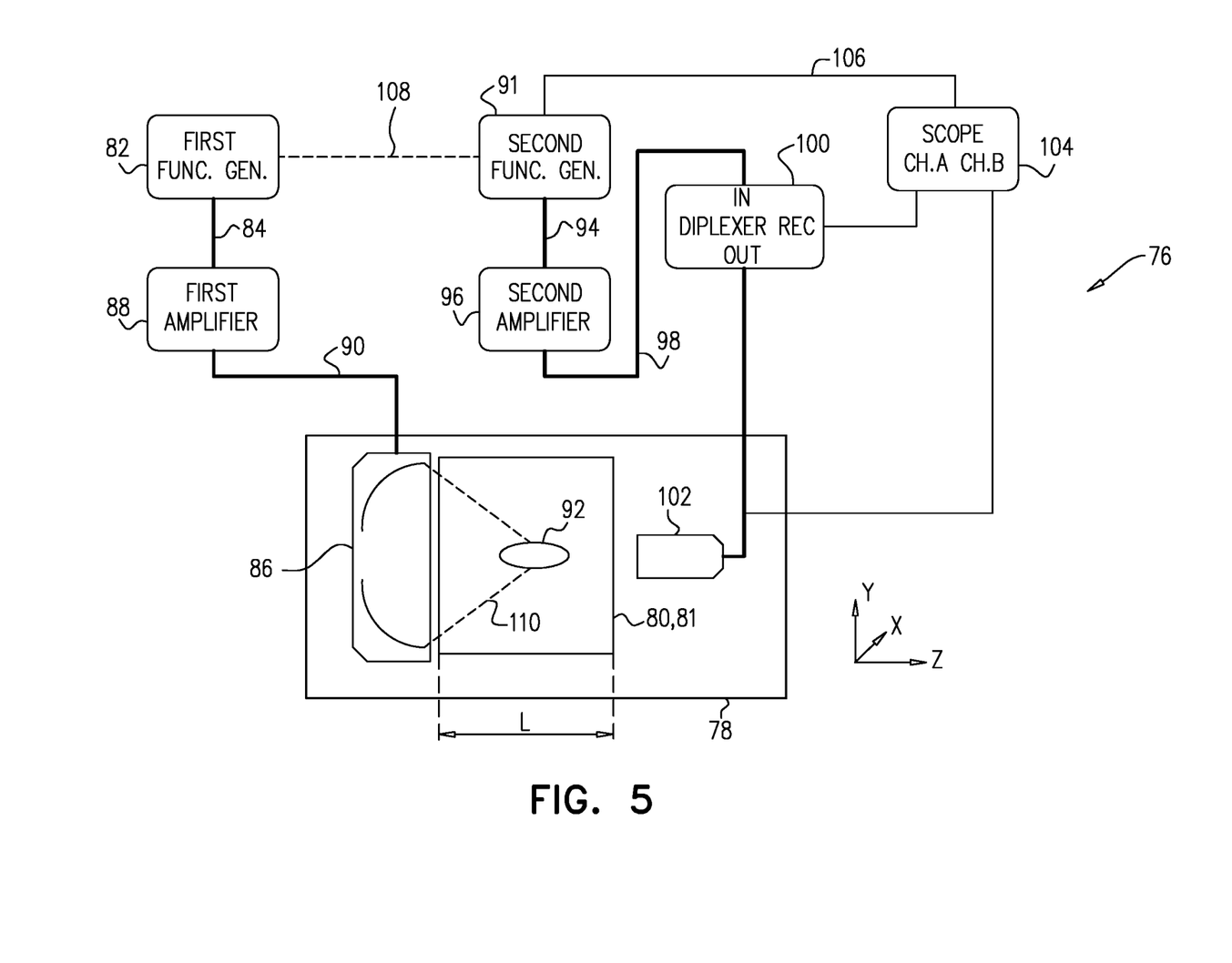
FIG. 5 is a schematic illustration of an experimental setup for an experiment carried out by the inventor, in accordance with some applications of the present invention.

Reference is now made to FIG. 5, which is a schematic illustration of an experimental setup 76 for an experiment carried out by the inventor, in accordance with some applications of the present invention. Setup 76 comprises a water tank 78, filled with degassed water. For clarity of explanation, a reference system is defined with the axes X, Y and Z, the Z axis being parallel to the length of the tank, the X axis being parallel to the width of the tank, and the Y axis being parallel to the height of the tank.

A cubic block of gelatin 80 is immersed and fixed in place inside the water tank. A side-length L of cubic block 80 is about 8 cm. Gelatin 80 will serve as a tissue-mimicking phantom 81 (hereinbelow "phantom"). There are many descriptions for the preparation of a phantom in the literature, in particular phantoms for acoustic and ultrasound experiments. For example, 60 grams of pure commercial gelatin (100% fish gelatin, Williger, Neto Group, Israel) in 520 ml of degassed water, and 4 grams of commercial corn-flour (Eshbal Functional Food Ltd., Kibbutz Maanit, Israel), rested overnight in the refrigerator (4 deg. C.).

A first function generator 82 generates a first signal 84, e.g., a sine-wave, at a first frequency. The first frequency should match a first transducer 86. Function generator 82 may generate a continuous-wave signal (CW) or pulsed wave signal. A first power amplifier 88, for example a class A, 50 dB gain amplifier, amplifies the signal. The amplified signal 90 drives first transducer 86. First transducer 86 comprises a matching network, designed to ensure good electrical impedance matching between first transducer 86 and first amplifier 88. First transducer 86 is acoustically coupled to the phantom 81, and for some applications, first transducer 86 may be adapted to be immersed in water tank 78. First transducer 86 is fixed in place and transmits acoustic energy 110 into phantom 81. In some applications, the direction of acoustic energy 110, generated by first transducer 86, is parallel to the Z axis. In some applications, acoustic energy 110 converges into one or more regions, forming a focal point 92 (hereinbelow 'focus') or other 'hotspots' in front of the first transducer 86 and inside phantom 81.

A second function generator 91 generates a second signal 94, e.g. a sine-wave at a second frequency which is higher than the first frequency. Second signal 94 may be a continuous wave signal or pulsed wave signal. A second power amplifier 96, for example a class A, 43 dB gain amplifier, amplifies second signal 94. The amplified signal 98 is received by a diplexer 100. Diplexer 100 is typically a passive device with three ports (marked IN, OUT, and REC). Diplexer 100 is used for pulse-echo setups and enables isolation of a sensitive receiving channel REC from the high-power excitation.

A second transducer 102 is used for pulse-echo. Second transducer 102 is acoustically coupled to phantom 81, and (a) transmits acoustic energy in pulses into the phantom 81 and (b) receives acoustic energy scattered and reflected from the phantom 81. Second transducer 102 may comprise a single piezo-electric element (other setups may comprise a double-element, linear-array, convex-array, two-dimensional array or other arrangement of piezo-electric transducers). In this configuration, second transducer 102 is adapted to provide A-Mode (one-dimensional) Doppler data, enabling to relate the received echo data to one-dimensional distance, Where spatial resolution is determined by pulse length and speed of sound. Second transducer 102 may be adapted to be immersed in water tank 78. Additionally or alternatively (and not shown in the figure), second transducer 102 may be mounted on a sliding frame, or a translating stage, with manual or electronic control, enabling to accurately shift the position of second transducer 102 relative to water tank 78. In principle, scanning along one dimension and recording multiple sets of A-Mode Doppler echo data can be useful to generate a two-dimensional map from multiple, evenly spaced, A-Mode Doppler echo data sets. In setup 76 an 'anti-parallel' configuration is described, where the angle between the first and second acoustic beams is 180 degrees.

A scope 104 is a device used for acquisition, recording, digitizing, storing and displaying the signals in two channels, marked. CH.A and CH.B. Channel A records the echo data from receiving channel REC of Diplexer 100, while Channel B records the transmitted pulse data, preferably through a ×10 voltage probe. Scope 104 is synchronized with second function generator 91 via a synchronized electrical connection 106. The timing for the acquisition is set by second function generator 91. The recorded echo data will be stored and processed off-line to extract the time-dependent Doppler shift and the related particle-velocity. Alternatively, scope 104 may be programmed to perform at least part of the data processing and to display results on a screen.

In a specific implementation of setup 76 the following were used:
Keysight 33522B, as first function generator 82,
Electronics & Innovation 2100L, as first power amplifier 88,
Sonic-Concepts H184-002, with the dedicated matching circuit box, as first transducer 86,
Keysight 33522B, as second function generator 91 (this is a dual-channel instrument which was used as both the first and second function generators)
Mini-Circuits LZY22+, as second power amplifier 96, Ritec RDX-6, as diplexer 100,
Olympus/Panametrics V312, as second transducer 102,
PicoScope 3204B, as scope 104,
a first frequency selected from 0.75 to 1 MHz, e.g. 1 MHz, and
a second frequency set to 10 MHz, with burst length of 20 cycles (pulse width of 2 microseconds)

Figure 4:
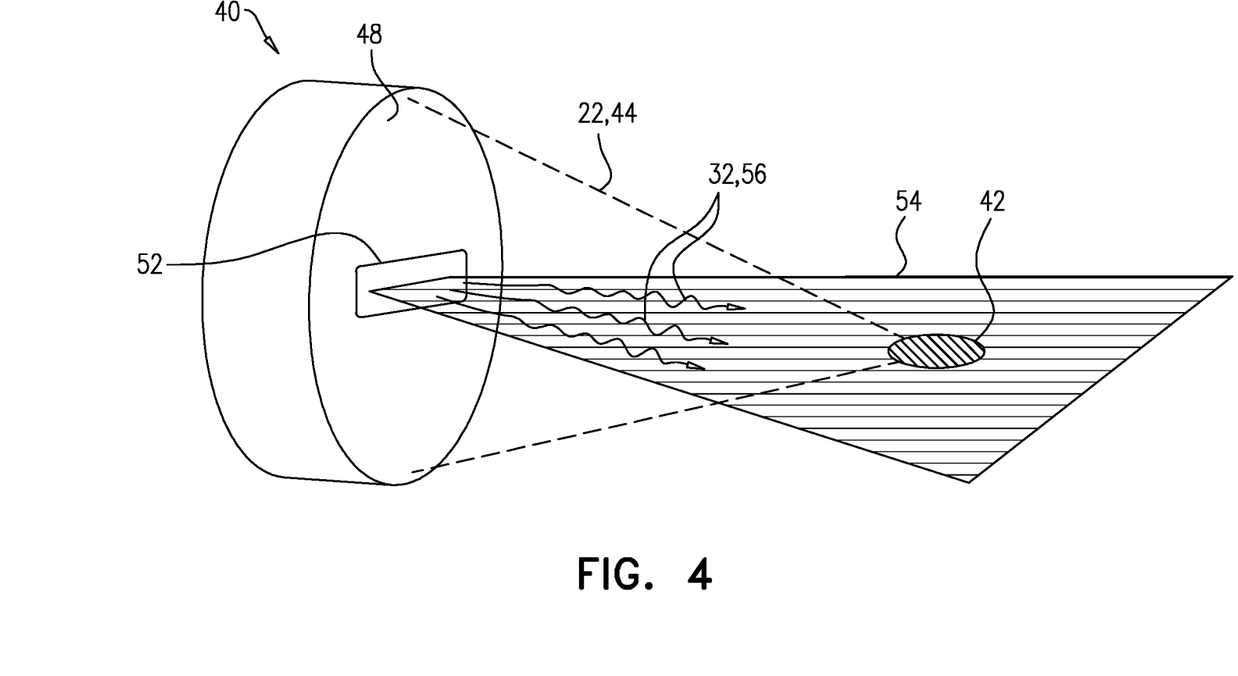
FIG. 4 is a schematic illustration of a HIFU transducer and acoustic probe disposed on a single unit, according to some applications of the present invention.

An alternative configuration is also described where the first and second acoustic beams are parallel, i.e., the angle between the first and second acoustic beams is substantially zero. First transducer 86 may be designed with a central hole and second transducer 102 is positioned behind first transducer 86 such that the two beams are aligned, such as is shown in FIG. 4. For example, Sonic-Concepts H184-002, as well as other models, have a central hole of diameter of about 40 mm. The clearance provided by the hole enables the second transducer to perform somewhat limited scanning inside the hole, while still providing data corresponding to the middle zone of the beam from first transducer 86.

For some applications, the two function generators 82 and 91 may be synchronized by an electrical connection 108 between them or by using a 2-channel instrument, e.g. Keysight 33522B, having a channel 1 for first signal 84 and a channel 2 for second signal 94. When first function generator 82 and second function generator 91 are synchronized, the first acoustic field may be pulsed as well, with tuned synchronization (a controlled time delay) between the two fields.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a focal region of high intensity focused ultrasound (HIFU) energy, the apparatus comprising:
   (A) an ultrasound transducer configured to generate a first acoustic field by emitting the HIFU energy into a region of a medium at a first frequency, the first acoustic field generating oscillatory motion of scatterers disposed within the medium in the region, the scatterers oscillating at the first frequency;
   (B) an acoustic probe,
      wherein the acoustic probe is configured to emit pulse-echo ultrasound energy into the medium at an imaging frequency,
      wherein an acoustic element is selected from the group consisting of the ultrasound transducer and the acoustic probe, and wherein the acoustic element is configured to generate a second acoustic field by transmitting a pulsed acoustic wave into the region at a second frequency,
      wherein the second frequency is higher than the first frequency and wherein the second acoustic field scatters off the scatterers at Doppler-shifted frequencies that are related to the oscillatory motion of the scatterers, resulting in echo data containing a time-dependent Doppler shift that oscillates at a frequency that is related to the first frequency, and
      wherein the acoustic probe is further configured to receive the echo data of the second acoustic field scattering off the scatterers; and
   (C) control circuitry configured to (a) synchronize the first and second acoustic fields such that the pulsed acoustic wave at the second frequency is transmitted into the region while the HIFU energy is being emitted into the region, (b) generate a real-time sonogram of the medium from reflections of the pulse-echo ultrasound energy, (c) extract the oscillating time-dependent Doppler shift from the received echo data, (d) convert the extracted Doppler shift into acoustic particle-velocity of the first acoustic field in the region, and (e) generate a map of acoustic particle-velocities of the first acoustic field on a portion of the sonogram corresponding to the region.

2. The apparatus according to claim 1, wherein the acoustic element comprises the ultrasound transducer.

3. The apparatus according to claim 1, wherein the acoustic element comprises the acoustic probe.

4. The apparatus according to claim 1, wherein the first frequency is 0.1-5 MHz.

5. The apparatus according to claim 1, wherein the second frequency is 3 to 25 times higher than the first frequency.

6. The apparatus according to claim 5, wherein the second frequency is 5 to 10 times higher than the first frequency.

7. The apparatus according to claim 1, wherein the medium is tissue of a body of a subject and wherein the transducer is configured to cause a therapeutic effect in the tissue by emitting the HIFU energy into the tissue.

8. The apparatus according to claim 7, wherein the transducer is configured to cause the therapeutic effect in the tissue by heating the tissue.

9. The apparatus according to claim 7, wherein the control circuitry is further configured to:
   monitor a change in a characteristic of the tissue by monitoring a time variation of the Doppler shift; and
   in response to the monitoring, terminate the first acoustic field when the characteristic of the tissue reaches a threshold value.

10. The apparatus according to claim 9, wherein the characteristic of the tissue is mechanical impedance of the tissue, and wherein the control circuitry is configured to (a) monitor a change in the mechanical impedance of the tissue by monitoring a time variation of the Doppler shift, and (b) in response to the monitoring, terminate the first acoustic field when the mechanical impedance of the tissue reaches a threshold value.

11. The apparatus according to claim 9, wherein the control circuitry is configured to monitor the change in the characteristic over a time period that is 1-120 seconds long.

12. The apparatus according to claim 7, wherein:
   the transducer is configured to operate in distinct calibration and therapy modes to facilitate application of therapeutic HIFU energy to a target location, in each of the modes emitting the HIFU energy with one or more differing respective parameters, and
   the control circuitry is configured to vary the one or more respective parameters such that when the transducer operates in the therapeutic mode the HIFU energy causes a therapeutic effect in the tissue whereas when the transducer is operating in the calibration mode the HIFU energy does not cause a therapeutic effect in the tissue.

13. The apparatus according to claim 12, wherein the control circuitry is configured to monitor the tissue when the transducer operates in the therapeutic mode and to vary the parameters of the therapeutic mode according to the monitoring in order to alter an effect on the tissue.

14. The apparatus according to claim 12, wherein the apparatus comprises a targeting unit configured to move the focal region of the HIFU energy.

15. The apparatus according to claim 14, wherein the targeting unit is configured such that manual movement of the targeting unit moves the focal region of the HIFU energy within the medium by moving the transducer with respect to the medium.

16. The apparatus according to claim 14, wherein the targeting unit comprises (i) a transducer controller and (ii) targeting circuitry configured to (a) obtain data corresponding to the focal region of the HIFU energy on the map of acoustic particle-velocities, (b) obtain data corresponding to a target location in the medium, and (c) send an electric signal to the transducer controller, wherein the transducer controller is configured to receive the electric signal and in response thereto move the focal region of the HIFU energy toward the target location within the medium.

17. The apparatus according to claim 16, wherein the transducer controller is configured to (a) move the focal region of the HIFU energy with respect to the transducer, and (b) change a size of the focal region of the HIFU energy by applying phased-array control to the HIFU energy emitted by the transducer.

18. The apparatus according to claim 16, wherein the transducer controller is configured to move the focal region of the HIFU energy by moving the transducer with respect to the medium.

19. The apparatus according to claim 1, further comprising a single housing to which the ultrasound transducer and the acoustic probe are coupled, wherein the housing aligns the first and second acoustic fields to be parallel or anti-parallel.

20. The apparatus according to claim 1, wherein the control circuitry is further configured to provide a controllable phase difference between the first and second acoustic fields by synchronizing the first and second acoustic fields.

* * * * *